(12) United States Patent
Baer et al.

(10) Patent No.: US 7,027,133 B2
(45) Date of Patent: Apr. 11, 2006

(54) AUTOMATED LASER CAPTURE MICRODISSECTION

(75) Inventors: Thomas M. Baer, Mountain View, CA (US); Norbert Hagen, Livermore, CA (US); Bruce J. Richardson, Los Gatos, CA (US); David R. Brewer, III, Aptos, CA (US); Lisa Reese, Felton, CA (US)

(73) Assignee: Arcturus Bioscience, Inc., Mountain View, CA (US)

( * ) Notice: Subject to any disclaimer, the term of this patent is extended or adjusted under 35 U.S.C. 154(b) by 0 days.

(21) Appl. No.: 10/989,206

(22) Filed: Nov. 15, 2004

(65) Prior Publication Data
US 2005/0089949 A1    Apr. 28, 2005

Related U.S. Application Data

(62) Division of application No. 10/735,111, filed on Dec. 12, 2003, now Pat. No. 6,870,625, which is a division of application No. 09/707,313, filed on Nov. 6, 2000, now Pat. No. 6,690,470.

(60) Provisional application No. 60/245,884, filed on Nov. 3, 2000, provisional application No. 60/163,634, filed on Nov. 4, 1999.

(51) Int. Cl.
G01N 1/00      (2006.01)

(52) U.S. Cl. ............................................... 356/36

(58) Field of Classification Search .................. None
See application file for complete search history.

(56) References Cited

U.S. PATENT DOCUMENTS

| 3,680,947 A | 8/1972 | Wanesky |
| 3,705,769 A | 12/1972 | Johannameier |
| 3,848,962 A | 11/1974 | Nelson |
| 4,210,384 A | 7/1980 | Meyer et al. |
| 4,303,866 A | 12/1981 | Porro et al. |
| 4,333,983 A | 6/1982 | Allen |
| 4,436,385 A | 3/1984 | Fischer et al. |
| 4,508,435 A | 4/1985 | Graham et al. |
| 4,509,834 A | 4/1985 | Hodgson |
| 4,538,885 A | 9/1985 | Graham et al. |
| 4,552,033 A | 11/1985 | Marzhauser |
| 4,600,282 A | 7/1986 | Yamamura et al. |
| 4,614,431 A | 9/1986 | Komeyama |

(Continued)

FOREIGN PATENT DOCUMENTS

CH         566 015         8/1975

(Continued)

OTHER PUBLICATIONS

Allred, D. Craig and Mohsin, Syed K. (2000). "Biological features of human premalignant breast disease," Chapter 24 in *Disease of the Breast*, 2nd ed., Jay R. Harris, ed., Lippicott Williams & Wilkins: Philadelphia, pp. 355-366.

(Continued)

*Primary Examiner*—Tu T. Nguyen
(74) *Attorney, Agent, or Firm*—Lukas IP Group; Rimas Lukas

(57) ABSTRACT

Systems and methods for automated laser capture microdissection are disclosed. High throughput microdissection is provided by using cell procurement and multi-imaging tools for pre-selecting cells of interest. Novel methods of computer-controlled cap transfer along with automated multi-slide and multi-cap placements, and automated slide and cap detection are provided. The systems and methods provide the advantages of increased speed and much lower rates of contamination.

5 Claims, 14 Drawing Sheets

U.S. PATENT DOCUMENTS

| | | |
|---|---|---|
| 4,623,839 A | 11/1986 | Garretson et al. |
| 4,627,009 A | 12/1986 | Holmes et al. |
| 4,672,559 A | 6/1987 | Jansson et al. |
| 4,673,261 A | 6/1987 | Hunt et al. |
| 4,684,781 A | 8/1987 | Frish et al. |
| 4,702,565 A | 10/1987 | Schilling et al. |
| 4,731,530 A | 3/1988 | Mikan |
| 4,760,385 A | 7/1988 | Jansson et al. |
| 4,807,984 A | 2/1989 | Kurimura et al. |
| 4,824,229 A | 4/1989 | Narita et al. |
| 4,836,667 A | 6/1989 | Ozeki |
| 4,852,985 A | 8/1989 | Fujihara et al. |
| 4,856,873 A | 8/1989 | Kleinberg |
| 4,871,245 A | 10/1989 | Ishikawa et al. |
| 4,920,053 A | 4/1990 | Inoue et al. |
| 4,923,294 A | 5/1990 | Courtenay |
| 4,954,715 A | 9/1990 | Zold |
| 4,964,708 A | 10/1990 | Mason |
| 4,987,006 A | 1/1991 | Williams et al. |
| 4,992,660 A | 2/1991 | Kobayashi |
| 5,017,428 A | 5/1991 | Mecke et al. |
| 5,029,791 A | 7/1991 | Ceccon et al. |
| 5,057,689 A | 10/1991 | Nomura et al. |
| 5,077,620 A | 12/1991 | Mauro |
| 5,089,909 A | 2/1992 | Kleinberg |
| 5,103,338 A | 4/1992 | Crowley et al. |
| 5,126,877 A | 6/1992 | Biber |
| 5,143,552 A | 9/1992 | Moriyama |
| 5,162,941 A | 11/1992 | Favro et al. |
| 5,165,297 A | 11/1992 | Krueger |
| 5,173,802 A | 12/1992 | Heller |
| 5,173,803 A | 12/1992 | Heller |
| 5,225,326 A | 7/1993 | Bresser et al. |
| 5,253,110 A | 10/1993 | Ichihara et al. |
| 5,262,891 A | 11/1993 | Nakasato |
| 5,263,384 A | 11/1993 | Suzuki |
| 5,280,384 A | 1/1994 | Shibasaki |
| 5,288,996 A | 2/1994 | Betzig et al. |
| 5,296,963 A | 3/1994 | Murakami et al. |
| 5,298,963 A | 3/1994 | Moriya et al. |
| 5,312,393 A | 5/1994 | Mastel |
| 5,323,009 A | 6/1994 | Harris |
| 5,337,178 A | 8/1994 | Kung et al. |
| 5,345,333 A | 9/1994 | Greenberg |
| 5,357,366 A | 10/1994 | Marchlenski |
| 5,359,417 A | 10/1994 | Muller et al. |
| 5,367,401 A | 11/1994 | Saulietis |
| 5,378,675 A | 1/1995 | Takeyama et al. |
| 5,386,112 A | 1/1995 | Dixon |
| 5,393,647 A | 2/1995 | Neukermans et al. |
| 5,403,970 A | 4/1995 | Aoki |
| 5,412,503 A | 5/1995 | Nederlof |
| 5,420,716 A | 5/1995 | Fukaya |
| 5,434,703 A | 7/1995 | Morizumi |
| 5,450,233 A | 9/1995 | Yamamoto et al. |
| 5,455,420 A | 10/1995 | Ho et al. |
| 5,468,967 A | 11/1995 | Chan et al. |
| 5,471,260 A | 11/1995 | Luce et al. |
| 5,479,252 A | 12/1995 | Worster et al. |
| 5,492,861 A | 2/1996 | Opower |
| 5,504,366 A | 4/1996 | Weiss et al. |
| 5,506,725 A | 4/1996 | Koike et al. |
| 5,510,615 A | 4/1996 | Ho et al. |
| 5,517,353 A | 5/1996 | Ikoh et al. |
| 5,532,128 A | 7/1996 | Eggers et al. |
| 5,532,476 A | 7/1996 | Mikan |
| 5,532,873 A | 7/1996 | Dixon |
| 5,535,052 A | 7/1996 | Jorgens |
| 5,536,941 A | 7/1996 | Swann |
| 5,537,863 A | 7/1996 | Fujiu et al. |
| 5,552,928 A | 9/1996 | Furuhashi et al. |
| 5,556,790 A | 9/1996 | Pettit |
| 5,557,456 A | 9/1996 | Garner et al. |
| 5,558,329 A | 9/1996 | Liu |
| 5,559,329 A | 9/1996 | Joseph et al. |
| 5,578,832 A | 11/1996 | Trulson et al. |
| 5,587,748 A | 12/1996 | Luce et al. |
| 5,587,833 A | 12/1996 | Kamentsky |
| 5,598,888 A | 2/1997 | Sullivan et al. |
| 5,602,674 A | 2/1997 | Weissman et al. |
| 5,619,035 A | 4/1997 | Weiss et al. |
| 5,621,207 A | 4/1997 | O'Mara |
| 5,631,734 A | 5/1997 | Stern et al. |
| 5,638,206 A | 6/1997 | Sumiya et al. |
| 5,659,421 A | 8/1997 | Rahmel et al. |
| 5,707,801 A | 1/1998 | Bresser et al. |
| 5,728,527 A | 3/1998 | Singer et al. |
| 5,751,839 A | 5/1998 | Drocourt et al. |
| 5,843,644 A | 12/1998 | Liotta et al. |
| 5,843,657 A | 12/1998 | Liotta et al. |
| 5,859,699 A | 1/1999 | Baer et al. |
| 6,010,888 A * | 1/2000 | Liotta et al. ............... 435/100 |
| 6,143,535 A * | 11/2000 | Palsson ................ 435/173.1 |
| 6,184,973 B1 | 2/2001 | Baer et al. |
| 6,204,030 B1 | 3/2001 | Liotta et al. |
| 6,215,550 B1 | 4/2001 | Baer et al. |
| 6,226,392 B1 | 5/2001 | Bacus et al. |
| 6,569,639 B1 | 5/2003 | Liotta et al. |

FOREIGN PATENT DOCUMENTS

| | | |
|---|---|---|
| DE | 1 263 339 | 3/1968 |
| DE | 196 03 996 | 8/1997 |
| EP | 0 748 439 | 7/1999 |
| WO | WO 91/07683 | 5/1991 |
| WO | WO 94/02646 | 2/1994 |
| WO | WO 95/23960 | 9/1995 |
| WO | WO 95/30919 | 11/1995 |
| WO | WO 97/13838 | 4/1997 |
| WO | WO 98/35216 | 8/1998 |
| WO | 98/44446 | 10/1998 |
| WO | WO 99/19341 | 4/1999 |
| WO | WO 99/45094 | 9/1999 |
| WO | WO 00/34756 | 6/2000 |
| WO | WO 00/34757 | 6/2000 |

OTHER PUBLICATIONS

Ashkin, A. and Dziedzic, J.M. (1989). "Internal cell manipulation using infrared laser traps," 86:7914-7918.

Bonner, Robert F. et al. (Nov. 21, 1997). "Laser capture microdissection: Molecular analysis of tissue," *Science* 278: 1481-1482.

Emmert-Buck, Michael R. et al. (1996). "Laser capture microdissection," *Science* 274:998-1001.

Friend, Tim (Aug. 5, 1997). "Getting up close to cancer genes," printed in *USA Today* newspaper, Science section, page 4D.

Fukcui, K. et al. (Jun. 1992). "Microdissection of plant chromosomes by argon-ion laser beam," *Theoretical & Applied Genetics* 84:787-791.

Goldstein, Seth R. et al. (1998). "Thermal modeling of laser capture microdissection," *Applied Optics* 37(31):7378-7391.

Harlow and Lane, eds. (1988). *Antibodies:A Laboratory Manual* Cold Spring Harbor, New York: pp. iii-ix (Table of Contents).

Heng, Henry H.Q. et al. (1992). "High-resolution mapping of mammalian genes by in situ hybridization to free chromatin," *Proc. Natl. Acad. Sci. USA* 89:9509-9513.

Isenberg, G. et al. (1976). "Cell surgery by laser microdissection: a preparative method," *J. Microsc.* 107(Pt 1):19-24.

U.S. Appl. No. 09/018,452, filed Feb. 4, 1998, Baer et al.
U.S. Appl. No. 09/121,677, filed Jul. 23, 1998, Baer et al.
U.S. Appl. No. 09/121,691, filed Jul. 23, 1998, Baer et al.
U.S. Appl. No. 09/617,742, filed Jul. 17, 2000, Baer et al.
U.S. Appl. No. 09/706,332, filed Nov. 3, 2000, Baer et al.

Jiménez, C. R. et al. (1994). "Neuropeptide expression and processing as revealed by direct matrix-assisted laser desorption ionization mass spectrometry of single neurons," *Journal of Neurochemistry* 62(1):404-407.

Kubo, Yoshiaki et al. (Mar. 1, 1995). "Early detection of Knudson's two-hits in preneoplastic renal cells of the Eker rat model by the laser microdissection procedure," *Cancer Research* 55(5):989-990.

Kuska, Bob (1996). "New aim-and-shoot technique speeds up cell analysis," *J. Natl. Cancer Inst.* 88(23):1708-1709.

Lawrence, Jeanne Bentley et al. (1998). "Sensitive, high-resolution chromatin and chromosome mapping in situ: Presence and orientation of two closely integrated copies of EBV in a lymphoma line," *Cell* 52:51-61.

Lewis, Ricki (Nov./Dec. 1998). "Laser aids Alzheimer's study," *Biophotonics International,* 2 pages total.

Lichter, Peter et al. (1990). "High-resolution mapping of human chromosome 11 by in situ hybridization with cosmid clones," *Science* 247:64-69.

Manuelidis, L. et al. (1990). "High-resolution mapping of satellite DNA using biotin-labeled DNA probes," *The J. Cell. Biol.* 95:619-625.

Meier-Ruge, W. et al. (1976). "The laser in the Lowery technique for microdissection of freeze-dried tissue slices," *Histochemical Journal* 8:387-401.

Schindler, Melvin et al. (Jul. 1985). "Automated analysis & survival selection of anchorage-dependent cells under normal growth conditions," *Cytometry* 6(4):368-374.

Schindler, Melvin (Aug. 1998). "Select, microdissect & eject," *Nature Biotechnology* 16:719-720.

Schütze, Karin and Lahr, Georgia (Aug. 1998). "Identification of expressed genes by laser-mediated manipulation of single cells," *Nature Biotechnology* 16:737-742.

Simone, Nicole L. et al. (Jul. 1998). "Laser capture microdissection: Opening the microscopic frontier to molecular analysis," *Trends Genet.* 14(7):272-276.

van den Engh, Ger et al. (1992). "Estimating genomic distance from DNA sequence location in cell nuclei by a random walk model," *Science* 257:1410-1412.

Veigel, Claudia et al. (1994). "New cell biological applications of the laser microbeam technique: the microdissection and skinning of muscle fibers and the perforation and fusion of sacrolemma vesicles," *European Journal of Cell Biology* 63:140-148.

* cited by examiner

AUTOMATED LASER CAPTURE MICRODISSECTION

CROSS-REFERENCE TO RELATED APPLICATION

This application is a divisional of U.S. application Ser. No. 10/735,111 filed Dec. 12, 2003 is now U.S. Pat. No. 6,870,625 which is a divisional of U.S. application Ser. No. 09/707,313, filed Nov. 6, 2000 now U.S. Pat. No. 6,690,470 and claims priority to U.S. Provisional Application No. 60/163,634, filed Nov. 4, 1999, and of U.S. Provisional Application No. 60/245,884, filed Nov. 3, 2000 entitled "Automated Laser Capture Microdissection" by the same inventors, the entire contents of all of these documents are hereby incorporated herein by reference as if fully set forth herein.

BACKGROUND OF THE INVENTION

Field of the Invention

The invention relates generally to the field of laser capture microdissection (LCM). More particularly, the invention relates to an automated system for performing LCM. Specifically, preferred embodiments of the invention relate to an automated LCM system that includes an automated single cell and tissue area targeting capability based on fluorescence labeling and image analysis, an automated cap arm mechanism, a road map camera, and a virtual joystick.

Laser capture microdissection (LCM) is a rapid, reliable method for procuring pure populations of targeted cells from specific microscopic regions of tissue sections for subsequent analysis. LCM-based molecular analysis of histopathological lesions can be applied to any disease process that is accessible through tissue sampling. Examples include mapping the field of genetic changes associated with the progression of microscopic premalignant cancer lesions; analysis of gene expression patterns in multiple sclerosis, atherosclerosis and Alzheimer's disease plaques; infectious microorganism diagnosis; typing of cells within disease foci; and analysis of genetic abnormalities in utero from selected rare fetal cells in maternal fluids.

The LCM technique is generally described by Emmert-Buck et al., Science 274, 998 (1996), the entire contents of which are incorporated herein by reference. The purpose of the LCM technique is to provide a simple method for the procurement of selected human cells from a heterogeneous population contained on a typical histopathology biopsy slide. In an LCM method, a transfer surface is placed onto the tissue section and then focally bonded to the targeted tissue, allowing it to be selectively removed for molecular analysis. In the microscope, the operator views the tissue and selects microscopic clusters of cells for analysis, then activates a laser within the microscope optics. The pulsed laser beam is absorbed within a precise spot on the transfer film immediately above the targeted cells. At this precise location, the film melts and fuses with the underlying cells of choice. When the film is removed, the chosen cells remain bound to the film, while the rest of the tissue is left behind.

LCM offers the advantage of transferring cells of interest to the polymer film in one step. The separate fragmentation step used in conventional microdissection and the resulting contaminating debris are avoided. In addition, only the targeted cells are affected such that the remaining tissue on the slide is fully accessible for further capture, allowing comparative molecular analysis of adjacent cells. The exact morphology of the procured cells is retained and held on the transfer film. In contrast to manual microdissection where cells may be pulverized or lost, the procurement of specific cells from a complex tissue section by LCM is reduced to a routine method amenable to widespread research and clinical diagnostic use.

In a manually operated laser capture microdissection system, the operator looks through a microscope at a tissue biopsy section mounted on a standard glass histopathology slide, which typically contains groups of cells. A thermoplastic film is placed over and in contact with the tissue biopsy section. Upon identifying a cell, or group of cells, of interest within the tissue section, the operator centers them in a target area of the microscope field and then generates a pulse from a laser such as a carbon dioxide laser having an intensity of about 50 milliwatts (mW) and a pulse duration of between about 50 to about 500 milliseconds (mS). The laser pulse causes localized heating of the plastic film as it passes through it, imparting to it an adhesive property. The cells then stick to the localized adhesive area of the plastic tape directly above them, whereupon the cells are extracted and readied for analysis. Because of the small diameter of the laser beam, extremely small clusters of cells may be microdissected from a tissue section.

By taking only these target cells directly from the tissue sample, researchers can immediately analyze the gene and enzyme activity of the target cells using other research tools. Such procedures as polymerase chain reaction amplification of DNA and RNA, and enzyme recovery from the tissue sample have been demonstrated. No limitations have been reported in the ability to amplify DNA or RNA from tumor cells extracted with laser capture microdissection.

A typical tissue biopsy sample consists of a 5 to 10 micron slice of tissue that is placed on a glass microscope slide using techniques well known in the field of pathology. This tissue slice is a cross section of the body organ that is being studied. The tissue consists of different types of cells. Often a pathologist desires to remove only a small portion of the tissue for further analysis.

SUMMARY OF THE INVENTION

A method for automating a laser capture microdissection is provided comprising providing a fluorescently-labeled tissue sample on a microscope slide, wherein the fluorescent label on the tissue corresponds to a biological property of interest; providing a source of fluorescent excitation, wherein an excitation beam emitted by the source is of an intensity and wavelength to excite a fluorescent label associated with the labeled tissue sample; exciting the tissue sample with the excitation beam and recording at least one information corresponding to an excitation pattern of the tissue sample; selecting from the recorded information, at least one section of the tissue sample for capture by laser capture microdissection; and targeting a laser for selectively capturing the at least one section of the tissue sample by laser capture microdissection.

In the method the at least one information corresponding to an excitation pattern of the tissue sample is a set of positional coordinates of sections of the tissue sample with increased fluorescence. The source of fluorescent excitation can be an episcopic (EPI) laser lamp. The method may further comprise: analyzing the captured image of the fluorescent tissue sample by scanning the image for locations of enhanced fluorescence; and responsive to the scanned information, selecting one or more sections of the tissue sample for laser capture microdissection.

In another aspect the method comprises analyzing the captured image of the fluorescent tissue sample by displaying the image in a video monitor; and selecting locations of enhanced fluorescence on the tissue sample by inputting a selection into an I/O device.

One embodiment of the invention provides an automated cap transfer system comprising a horizontal bar coupled to a main support bar by a vertical lead screw, whereby operation of the lead screw actuates a vertical displacement of the horizontal bar relative to the support bar; a fork coupled to the horizontal bar, the fork having two or more arms for engaging a LCM cap; a pivotable weight coupled to the horizontal bar, wherein the weight is seated on an engaged LCM cap; a lever coupled to the horizontal bar, the lever comprising at least one pin for engaging the weight and a pivot axis; a kick bar coupled to the support bar, whereby lowering the horizontal bar causes the kick bar to engage the lever and actuate a pivot of the lever about the pivot axis thereby causing the at least one pin of the lever to engage the weight and displace the weight relative to the cap.

In another aspect, an automated method of cap transfer in a LCM is provided comprising providing a work surface comprising a translation stage for performing LCM; providing a cap transfer arm coupled to the work surface for removably engaging a LCM cap; providing a controller coupled to a memory for receiving and storing an information corresponding to one or more locations on the work surface; and operating a movement of the cap transfer arm to place and remove a cap from one or more locations on the work surface.

Figure 1:
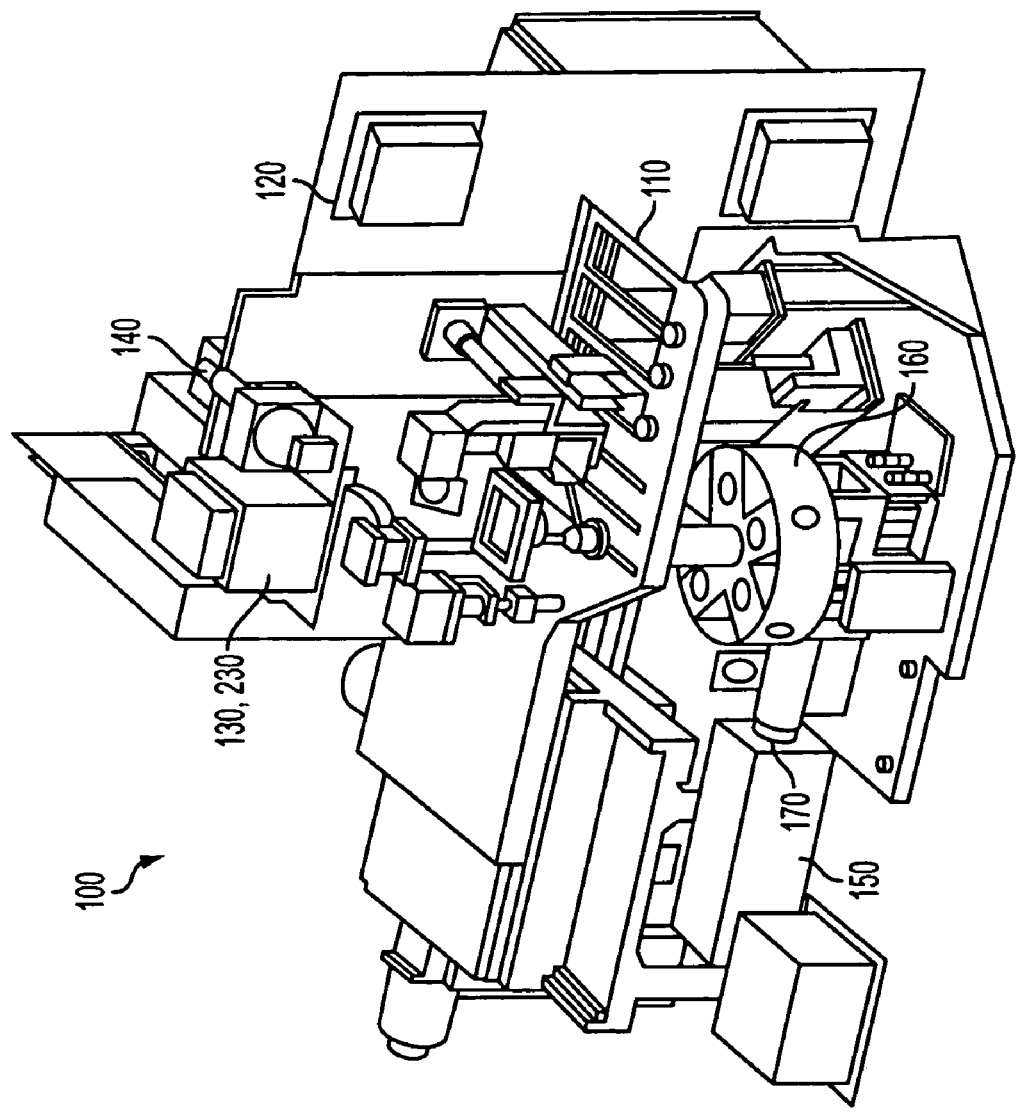
FIG. 1 illustrates a perspective view of an automated LCM device.

While the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DESCRIPTION OF THE INVENTION

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The entire contents of U.S. Ser. No. 09/018,452, filed Feb. 4, 1998, now U.S. Pat. No. 6,469,779, entitled "Laser Capture Microdissection Device"; U.S. Ser. No. 09/121,691, filed Jul. 23, 1998; U.S. Ser. No. 09/121,635, now U.S. Pat. No. 6,215,550, filed Jul. 23, 1998; U.S. Ser. No. 09/058,711, now U.S. Pat. No. 6,184,973, filed Apr. 10, 1998; and U.S. Ser. No. 09/121,677, filed Jul. 23, 1998; U.S. Ser. No. 09/617,742, now U.S. Pat. No. 6,512,576, filed Jul. 17, 2000 and U.S. Provisional Application No. 60/163,634 filed Nov. 4, 1999 are hereby expressly incorporated by reference into the present application as if fully set forth herein.

A non-automated LCM device operates to carry out the following general steps. A tissue or smear fixed on a standard microscope slide by routine protocols is introduced into an LCM and the tissue is placed adjacent a transfer film carrier cap which further ensures that transfer film stays out of contact with the tissue at this stage. Upon visualizing the tissue by a microscope, a user may select a region for microdissection. The selected section of the tissue is captured by pulsing with a low power infrared laser which activates the transfer film which then expands down into contact with the tissue. The desired cell(s) adhere to the transfer film. Microdissection is completed by lifting the film carrier, with the desired cell(s) attached to the film surface while the surrounding tissue remains intact. Extraction and subsequent molecular analysis of the cell contents, DNA, RNA or protein, are then carried out by standard methods.

LCM employs a thermoplastic transfer film that is placed on top of the tissue sample. This film is manufactured containing organic dyes that are chosen to selectively absorb in the near infrared region of the spectrum overlapping the emission region of common AlGaAs laser diodes. When the film is exposed to the focused laser beam the exposed region is heated by the laser and melts, adhering to the tissue in the region that was exposed. The film is then lifted from the tissue and the selected portion of the tissue is removed with the film. Thermoplastic transfer films such as a 100 micron thick ethyl vinyl acetate (EVA) film available from Electroseal Corporation of Pompton Lakes, N.J. (type E540) have been used in LCM applications. The film is chosen due to its low melting point of about 90° C.

The present invention reduces the manual labor and resulting inaccuracies from microdissection by automating several stages of the LCM process. The automation devices of the present invention greatly enhances the efficiency and precision of the process and also enables the execution of microdissection with greater accuracy, speed and sensitivity. High throughput microdissection is provided by using cell procurement and multi-imaging tools for pre-selecting cells of interest. Furthermore, novel methods of computer-controlled cap transfer along with automated multi-slide and multi-cap placements, automated slide and cap detection are provided.

As described in the following descriptions and accompanying diagrams, components involved in the automation include, but are not limited to, automated film carrier cap handling including the ability to process multiple slides simultaneously; automated tissue targeting and microdissection based on fluorescence labeling and image analysis; virtual imaging of a roadmap of the tissue for precise manipulation of the laser capture system which is turn enhanced by inclusion of a virtual joystick for navigating the virtual roadmap of the tissue; capability of imaging a full slide including markers or labels on the slide at up to about 1000× magnification; and software for controlling the manipulation of the various systems.

Turning to FIG. 1, a perspective view of an automated LCM device 100 is depicted. The automated LCM device 100 includes a variety of subsystems particularly adapted for the LCM technique which combine to provide synergistic and unexpectedly good results.

A work surface with a motorized translation stage 110 capable of simultaneously handling multiple tissue biopsy slides is coupled to an automated cap handling system 120. An optical train comprising a white light illumination system 130 and a laser source 140 operates to effect the laser guided microdissection. A fluorescent laser source 150 and a fluorescent filter wheel system 160 implements a fluorescent-detected tissue image analysis system which comprises one embodiment of the automated LCM process. In the depicted embodiment, a black-and-white and/or color camera housing system 170 generates static roadmap and live images of the tissue sample for added controllability during the LCM process.

Figure 2:
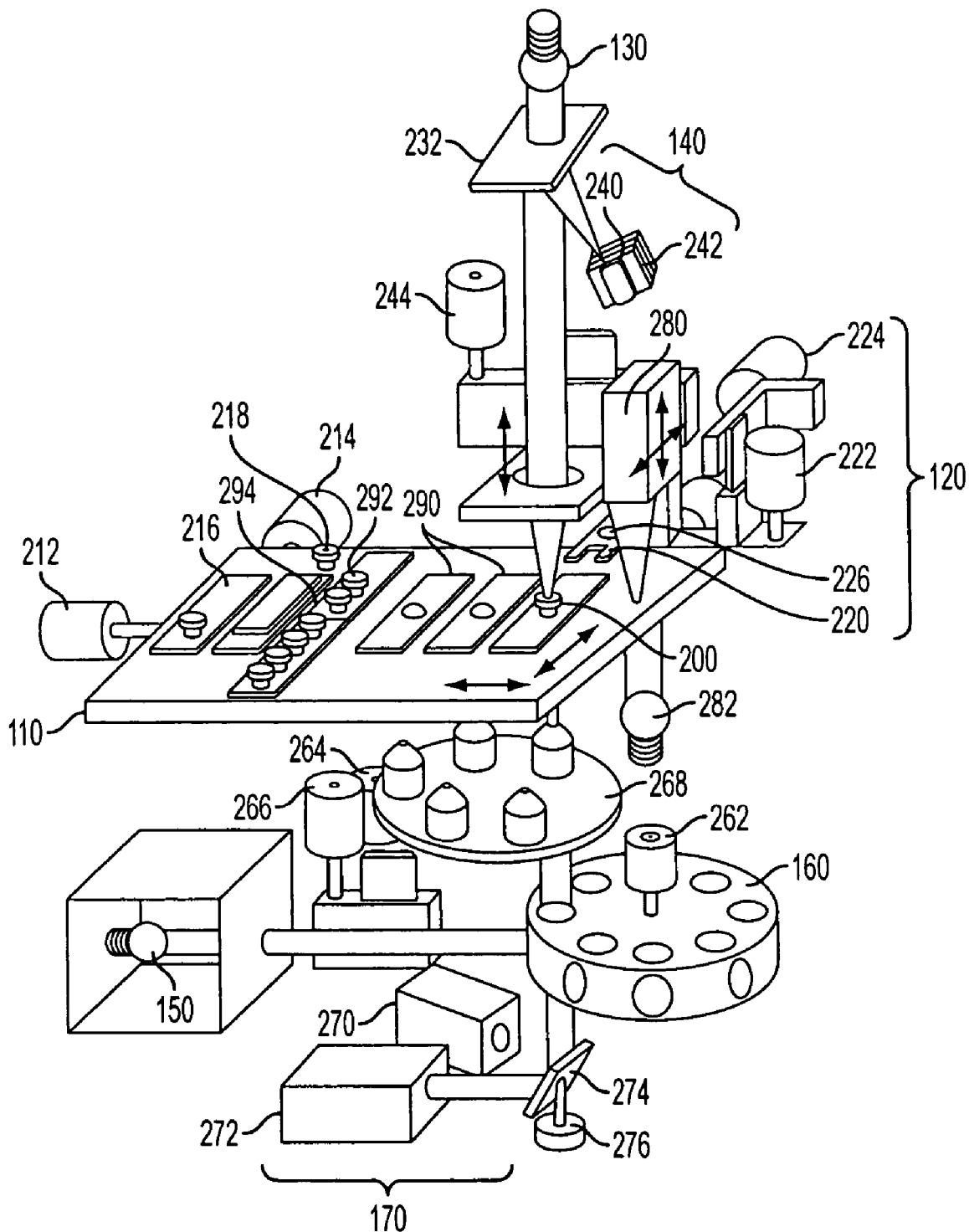
FIG. 2 illustrates a top level block diagram of the components of an automated LCM.

Turning now to FIG. 2, a top level block diagram of the components of an automated LCM and an embodiment of the relative arrangement of various novel parts of the system is depicted. The work surface 110 includes a translation stage to allow manipulation in an X-Y plane by a lateral translation motor 212 and a fore-and-aft translation motor 214. The work surface 110 also includes an output station 216 and a quality control station 218. One or more slides 290 of tissue samples can be simultaneously processed in a work surface 110 which may also include slides 294 which serve as staging areas for caps 292.

A cap transfer mechanic subassembly 120 is coupled to the work surface 110 and comprises a cap translation motor 224 which operates to move a cap lift fork 220 in and out of the work surface 110. The cap transfer system 120 also includes a visualizer filter 226 and a cap lift motor 222. The visualizer is a piece of diffuser glass positioned above tissue sample. The light from above is diffused by the visualizer 226 illuminating the sample from all angles from above. This high illumination angle or high NA (Numerical Aperture) illumination gives the best image quality. The visualizer 226 can be moved in and out of position and is located on the cap arm. The cap operation and components of the cap transfer system is discussed in further detail in a following section.

In general, any suitable scattering media can be used to provide the functions of the visualizer 226. Providing such a scattering media near the tissue to scatter the light results in dramatically improved illumination of the sample and much better visualization. A scattering media of this type eliminates the need for refractive index matching of the sample. Such a scattering media can allow visualization of the cell nucleus and other subcellular structures that would normally be obscured by normal illumination techniques. The scattering media can be a diffuser material. A diffuser material that is suitable for use as the scattering media is milk or opal glass which is a very dense, fine diffuser material. For instance, a suitable milk glass is available from Edmund Scientific as Part No. P43,717. Standard laser printer/photocopier paper can even be used as the scattering media. Other types of transparent scattering media can be used, such as, for example, frosted glass, a lenticular sheet, a volume diffuser, and/or a surface diffuser. In any event, the scattering media should be a material that aggressively scatters the illumination light. A single sheet of typical ground glass is generally inadequate and needs to be combined in multiple layers as a serial stack of three or four sheets of ground glass to diffuse the illumination light sufficiently can be directly or indirectly connected to the transfer film carrier and/or the LCM transfer film. Alternatively, the visualizer 226 can be formed on a surface of, or the interior of, the transfer film carrier and/or the LCM transfer film. The scattering media can be fabricated so as to shape the LCM beam and/or the illumination beam. The scattering media needs to be within a few millimeters of the sample to be effective. A few millimeters means less than one centimeter, preferably less than five millimeters.

The cap transfer mechanic subassembly 120 provides a structure for picking a microcentrifuge tube cap 292 from a supply 218 and placing the microcentrifuge tube cap 292 on top of a tissue sample on a slide 290 that is to undergo LCM. In the depicted embodiment, the microcentrifuge tube cap 292 is a cylindrical symmetric plastic cap and the supply 294 includes four consumables per slide 294. In the depicted embodiment, there is a laser capture microdissection transfer film coupled to the bottom of the microcentrifuge tube cap 120. The movement of the cap handling mechanic subassembly 120 is described in greater detail in a separate section.

A glass slide 290 to which the sample to be microdissected is fixed and upon which the microcentrifuge tube cap 292 is placed, is located in the primary optical axis of the automated LCM 100. In alternative embodiments, the slide that supports the sample can be made of other substantially transparent materials, for example, plastics such as polycarbonate. The glass slide 290 may be supported and held in place by a vacuum chuck (not shown). The vacuum chuck is a substantially flat surface that engages the glass slide 290 through a manifold (not shown) so as to hold the glass slide 290 in place while the microcentrifuge tube cap 120 is picked and placed and while the work surface 110 is manipulated in an X-Y plane.

The optical train comprises a white light illumination system 130 which is comprised of a condenser lamp 230 and a bandpass dichroic mirror 232. White light from the illuminator 230 passes downward toward the microcentrifuge tube cap 200 through a dichroic mirror 232 and a focusing lens (not shown). Also coupled to the optical train is a laser beam system 140 comprising a thermoelectric cooled 242 laser diode 240 with collimating optics emits a beam that is incident upon the dichroic mirror 232. The bandpass mirror 232 is a dichroic that reflects the beam downward through the focusing lens toward the microcentrifuge tube cap 200. Simultaneously, the dichroic mirror 232 allows white light from the illuminator 230 to pass directly down through the focusing lens toward the microcentrifuge tube cap 200. Thus, the laser beam and the white light illumination are superimposed. A laser focus motor 244 operates to control the focusing lens and adjust the laser beam spot size.

A schematic diagram of another component of an instrument according to the invention is depicted in FIG. 2. In this embodiment, a light source 150 (e.g., a fluorescence laser generated by an EPI/fluorescent xenon or mercury lamp), emits a specific wavelength or wavelength range. The specific wavelength or wavelength range of a beam emitted by the light source 150 is selected by a fluorescence filter wheel operated by a fluorescence filter changer motor 262, to excite a fluorescent system (e.g., chemical markers and optical filtering techniques that are known in the industry) that is incorporated in or applied to the sample to be microdissected. The frequency of the beam emitted by the fluorescence laser 150 can be tuned. The sample includes at least one member selected from the group consisting of chromophores and fluorescent dyes (synthetic or organic), and the process of operating the instrument includes identifying at least a portion of the sample with light that excites at least one member, before the step of transferring a portion of the sample to the laser capture microdissection transfer film. The fluorescent laser beam can be made coincident or coaxial with both the laser 240 beam path and the white light from illuminator 230 path. Fluorescence emitted by the sample beneath the microcentrifuge tube cap 200 is amplified (optionally) by an objective changer 268, reflected by a camera changer mirror and captured for "live" viewing by a camera system 170 which comprises a black-and-white camera 270 and/or a color camera 272. An objective changer motor 264 and a focus motor 266 operate to adjust the fluorescent laser beam and the emitted fluorescent beam. Optionally the objective changer may be implemented in the form of a wheel 268 to accommodate a multiplicity of objectives (five objectives, as depicted) for providing different amplifications of the fluorescent image for the cameras.

A road map camera system 280 is coupled to the work surface 110 and the cap transfer mechanic subassembly 120, and operates to provide an image of the tissue sample on the slide 290. The road map camera 280 is capable of translation to scan or otherwise provide an image of the tissue illuminated by a light source 282. Since the translation of the roadmap camera is coupled to the work surface 110, it allows for precise alignment of a selected section of the roadmap image to be brought into the path of the laser 240 beam. The section selected by a viewer of the road map camera image may be further viewed in an amplified form by a "live" viewer of the camera system 170 by selecting an appropriate objective from the objective changer 268 following alignment of the selected roadmap image to the fluorescent laser.

Figure 3A:
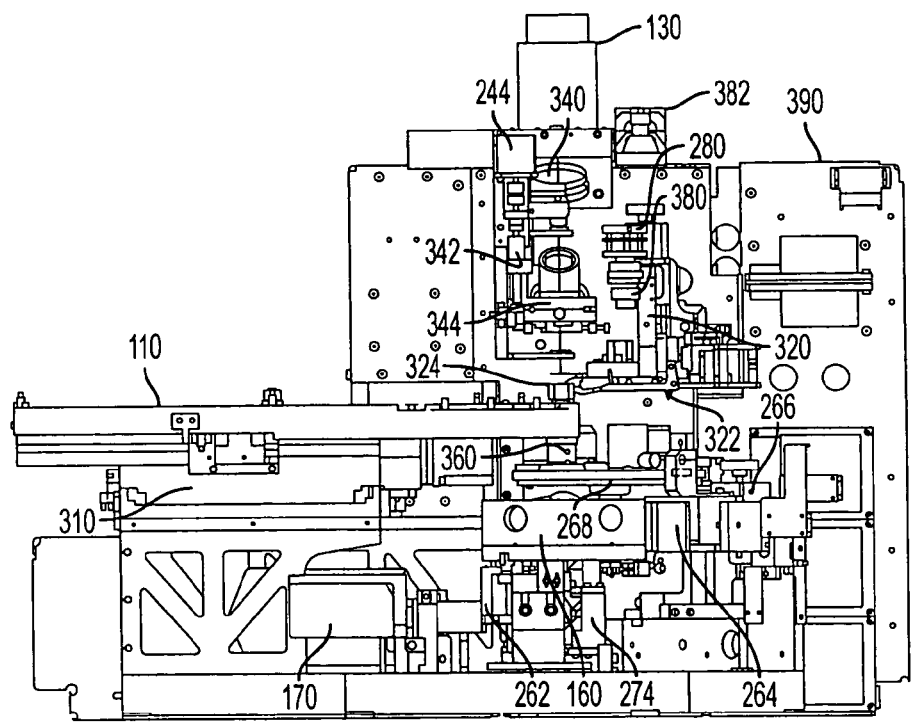
FIG. 3 illustrates a front view (FIG. 3a) and a side view (FIG. 3b) of a cross-section of an automated LCM.
Figure 3B:
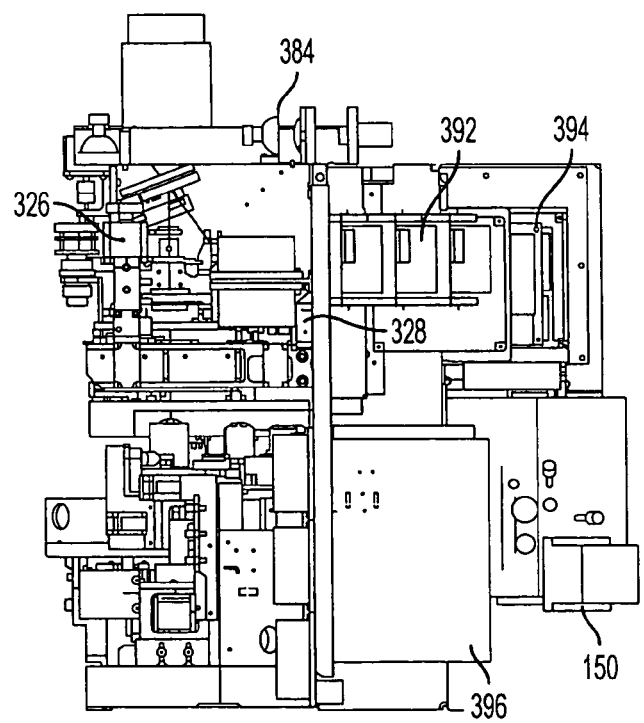

Turning now to FIG. 3, a front view (FIG. 3a) and a side view (FIG. 3b) of a cross-section of a depicted embodiment of an automated LCM are illustrated. An X-Y translation stage is coupled to the working surface 110. Further details of the cap transfer mechanic subassembly 120 are revealed including a cap arm assembly 320 comprising a cap arm kick bar 322 which operates a cap fork for transportation and operation of a cap and a cap arm weight 324 which operates to position the LCM film bearing cap on the sample as well as to insert a cap into a microcentrifuge tube or other consumable. Drive motors manipulate a cap arm vertically 326 and laterally 328 as depicted in FIG. 3b.

A laser beam focus lens assembly 344 operates to focus the LCM laser beam on the target sample slide and is manipulated by a laser focus lead screw 342 which is in turn adjusted by a laser focus motor 244. In idle mode, the laser beam path provides a visible low amplitude signal that can be detected via the image acquisition camera system 170 when a visual alignment is desired. In pulse mode, the laser beam path delivers energy to the microcentrifuge tube cap 200 and the optical characteristics of a cut-off filter attenuate the laser beam path sufficiently such that substantially none of the energy from the laser beam exits through the microscope.

Suitable laser pulse widths are from 0 to approximately 1 second, preferably from 0 to approximately 100 milliseconds, more preferably approximately 50 milliseconds. In a preferred embodiment the wavelength of the laser is 810 nanometers. In a preferred embodiment the spot size of the laser at the EVA material located on microcentrifuge tube cap 120 is variable from 0.1 to 100 microns, preferably from 1 to 60 microns, more preferably from 5 to 30 microns. These ranges are relatively preferred when designing the optical subsystem. From the standpoint of the clinical operator, the widest spot size range is the most versatile. A lower end point in the spot size range on the order of 5 microns is useful for transferring single cells.

Suitable lasers can be selected from a wide power range. For example, a 100 watt laser can be used. On the other hand, a 50 mW laser can be used. The laser can be connected to the rest of the optical subsystem with a fiber optical coupling. Smaller spot sizes are obtainable using diffraction limited laser diodes and/or single mode fiber optics. Single mode fiber allows a diffraction limited beam.

While the laser diode can be run in a standard mode such as $TEM_{oo}$, other intensity profiles can be used for different types of applications. Further, the beam diameter could be changed with a stepped lens in the lens assembly 344.

Changing the beam diameter permits the size of the portion of the sample that is acquired to be adjusted. Given a tightly focused initial condition, the beam size can be increased by defocusing. Given a defocused initial condition, the beam size can be decreased by focusing. The change in focus can be in fixed amounts. The change in focus can be obtained by means of indents on a movable lens mounting and/or by means of optical glass steps. In any event, increasing/decreasing the optical path length is the effect that is needed to alter the focus of the beam, thereby altering the spot size. For example, inserting a stepped glass prism into the beam so the beam strikes one step tread will change the optical path length and alter the spot size.

A series of microscope objectives 360 may be selectably deployed from an objective turret wheel 268 which is controlled by an objective wheel motor 264 while a second objective focus motor 266 operates to adjust the foci of objectives which have been positioned.

The road map camera 280 operates by one or more adjustable lens 380 and may include one or more of a top lamp 382 and a bottom lamp 384. The road map camera requires illumination from the top and the bottom for optimum imaging. The top illumination 382 is needed to illuminate identity markings on the slide. Typically a stick-on label is placed on one end of a slide and the label is marked with a pen and/or has a bar code printed on it. The top light source is used when the camera is over this portion of the slide. Optionally, a fiber optic is used to deliver light from the bottom of the slide. The bottom illumination 384 is used when the roadmap camera 280 is imaging tissue samples.

An electronics panel 390 comprises printed circuit boards 394 for controlling mechanics and instructions for the automated LCM, computer interface cards 392 and I/O devices 396 for communicating with a couples central processing unit may be assembled as part of the automated LCM unit 300.

1. Automated Fluorescent Microscopy

The procedure of selecting cells or specific regions of a sample for microdissection can be further automated by using fluorescently-stained cells. In image analysis, the labeled tissue is presented to an automated microscope on a solid substrate and the cells are detected through an analysis of the image formed by the microscope. Typically, the image is scanned with a small laser spot to excite the fluorescent molecules. The visual examination of the sample spread over a solid support with a microscope is a tedious, time consuming process. It is complicated by the presence of other fluorescent material. When searching abnormal cells with a microscope, a large surface has to be viewed, and the risk of missing one abnormal cell is high. The utilization of confocal microscopy or image analysis using fluorescent dyes permits the automated detection of the rare abnormal cells.

A rare cell of interest can be detected or identified on the basis of its morphological, biochemical, genetic, or other characteristics. Histochemical staining is especially useful for identification of a rare cell of interest. Immunological labeling is another method that can be used to identify a cell of interest. According to this technique, an antibody specific for an antigen whose presence (or absence) is characteristic of a rare cell of interest is bound to the cell and directly or indirectly labeled with a fluorescent stain. Immunolabeling techniques are well known and are described generally in Harlow and Lane, Antibodies: A Laboratory Manual, Cold Spring Harbor, N.Y. (1988), which is incorporated herein by reference.

The cell can be identified based on the density of stain resulting from a fluorescence-conjugated stain or by immunohistochemical methods using fluorescently-labeled antibodies. Cells extracted and stained in this manner are usually viewed using a microscope fitted with an appropriately colored filter. However detected, the location of the cell of interest on the support (e.g., slide) is determined and recorded.

In one aspect of the present invention, the cell is located on the slide by scanning an analyzed image and identifying the points of denser fluorescent label relative to the overall sample. This process is automated by a using a controller which scans the fluorescent sample and determines the positions (stage coordinates) of the cells or tissue section of note. In one embodiment, an automated microscope is used. In this embodiment, the microscope is equipped with a motorized stage, a computer based image analysis system (including algorithms for automated focusing and cell detection), and a means for storing the location (i.e., coordinates on the slide) of an identified rare cell, so that cells of interest can be precisely relocated. An example of an automated microscopes that includes a motorized stage is the LSC microscope (CompuCyte Corp., Cambridge Mass.). A typical embodiment of the automated navigation system according the invention comprises a fluorescent microscope, an automated XY stage, three chip color CCD camera and appropriate software. In another embodiment, the automated microscope may be replaced by an image scanner which records and analyzes a image of the slide to determine the coordinates of the cells of interest and then directs a controller to operate the microdissection process at the specified sites. In brief, the coordinates of a tissue section of interest are mapped by a controller after gathering data from the image capture system 170 the laser beam is aligned with the selected tissue section in reference to the coordinates of the translational stage 310 of the working surface 110. The size of tissue sections to be microdissected is preset in a totally automated system or may be selected by adjusting the focal characteristics of the laser beam.

The image analysis software typically includes a means for distinguishing a cell of interest from other cells in the population (e.g., by evaluation of the shape and size of the nucleus and cytoplasm, differential evaluation of images taken using different filters that reveal differences in cell staining) and for recording the location of the cell in the slide.

Techniques have been reported for the fluorescent visualization of molecules and complexes. Such techniques include such fluorescence microscopy-based techniques as fluorescence in situ hybridization (FISH; Manuelidis, L. et al., 1982, J. Cell. Biol. 95:619; Lawrence, C. A. et al., 1988, Cell 52:51; Lichter, P. et al., 1990, Science 247:64; Heng, H. H. Q. et al., 1992, Proc. Natl. Acad. Sci. U.S.A. 89:9509; van den Engh, G. et al., 1992, Science 257:1410). Fluorescence in situ hybridization refers to a nucleic acid hybridization technique which employs a fluorophor-labeled probe to specifically hybridize to and thereby, facilitate visualization of, a target nucleic acid. Such methods are well known to those of ordinary skill in the art and are disclosed, for example, in U.S. Pat. No. 5,225,326; U.S. patent application Ser. No. 07/668,751; PCT WO 94/02646, the entire contents of which are incorporated herein by reference. In general, in situ hybridization is useful for determining the distribution of a nucleic acid in a nucleic acid-containing sample such as is contained in, for example, tissues at the single cell level. Briefly, fluorescence in situ hybridization involves fixing the sample to a solid support and preserving the structural integrity of the components contained therein by contacting the sample with a medium containing at least a precipitating agent and/or a cross-linking agent. Alternative fixatives are well known to those of ordinary skill in the art.

A xenon or argon laser can be used to produce multiple lines for fluorescence excitation. A 355 line is useful for excitation of compounds such as DAPI and indo-1, while probes excited by a 488 line include FITC, phycoerythrin, and fluo-3. A wide variety of fluorescent probes and antibodies are available commercially. The Molecular Probes web site (www.probes.com) list a large number and Becton Dickinson (www.bdfacs.com) is a good resource for fluorescent antibodies.

2. Selection of Tissue Section

A slide carrying a fluorescently labeled tissue sample 290 is positioned on the working surface 110. The translation stage 310 operates to position the slide at a location for the performance of automated LCM. A controller (not shown) determines the X-Y coordinates (x, y) of the position of the slide. Confocal laser, fluorescence and illumination beams of the apparatus are aligned to pass through the same x,y coordinates on the working surface.

Optionally, the slide is first brought into alignment with a roadmap camera 280 by translating the x,y coordinates of the working surface into alignment with the focal plane and axis of the roadmap camera 280 and an image of the entire tissue sample is captured for reference. Image capture by the roadmap camera is aided by one or more lamps 382 and 384.

The slide is then aligned with the confocal axis of the illumination lamp 130 and the laser beam from the laser diode 240. The beam from the EPI/fluorescent lamp 150 is also aligned with the same optical axis to generate the fluorescent excitation of the tissue sample on the slide 290. A fluorescent filter wheel 160 may be used to select different lines for selective excitation of different fluorescent dyes used on a sample. The entire tissue sample or specific parts of it can be selectively excited by selecting different lenses of one or more objectives from an objective turret wheel 268.

A camera mirror 274 also aligned along the same optical axis reflects a "live" image of the illuminated fluorescent tissue and allows the capture of the "live" image in a black and white 270 or color 272 camera. A color CCD camera 272 is additionally able to distinguish different chrominance values resulting from different colored fluorescent emanations.

The "live" fluorescent image captured by the camera system 170 may be read automatically or displayed in the screen of a video terminal for precise selection of tissue sections of interest.

A typical embodiment of the fully automated navigation system according the invention comprises an image scanner and appropriate software. The x,y coordinates of a tissue section of interest (marked by enhanced fluorescence) are mapped by a controller after gathering scanned data from the image capture system 170. The automated cap transfer system, which is also coupled to the working surface 110, then positions a cap at the selected x,y coordinates of the working surface 110 in alignment with the laser beam. The translational stage 310 operates to align first the roadmap camera 280, and then the cap transfer system 120. A microprocessor implements the functions of the automated LCM for selecting tissue sections based on enhanced fluorescence. The x,y coordinates of a tissue section exhibiting enhanced fluorescence are recorded on a memory module and elements of the automated LCM apparatus such as the cap transfer arm and laser capture beam are aligned according to the recorded x,y coordinates. The microprocessor comprises a digital microprocessor or similar controller devices and other electronics such as display drivers and graphics chips necessary for controlling the automated LCM via an optional video display screen when additional control of the tissue section selection process is desired. The size of tissue sections to be microdissected may be preset in a totally automated system or may be manually selected by adjusting the focal characteristics of the laser beam. One or more image analysis softwares included in a memory of the microprocessor system typically includes instructions for distinguishing a cell of interest from other cells in the population (e.g., by evaluation of the shape and size of the nucleus and cytoplasm, differential evaluation of images taken using different filters that reveal differences in cell staining) and for recording the location of the cell in the slide.

3. Cap Transfer Arm

Figure 4:
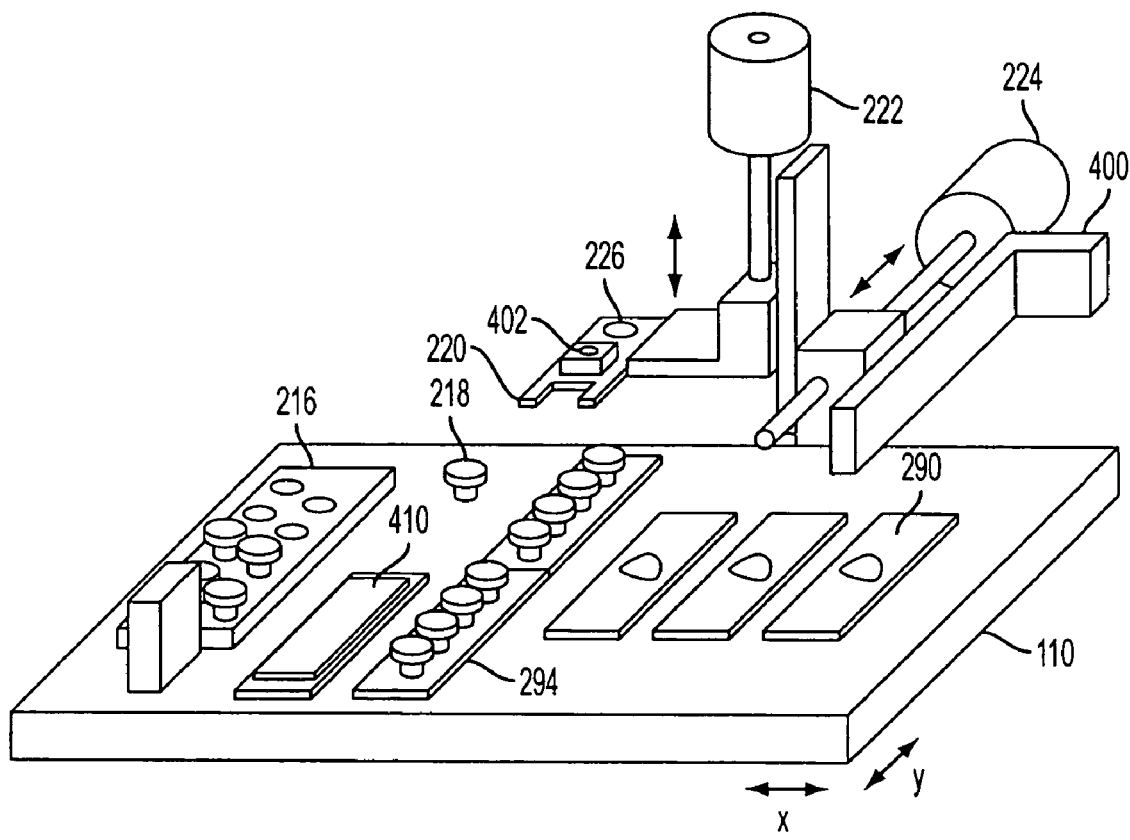
FIG. 4 illustrates a top level block diagram of a cap arm mechanism.

A cap arm mechanism, as illustrated in a top level block diagram in FIG. 4, is used to move the caps to different locations on the work surface. The automated LCM is able to manipulate cap arms and process multiple sample slides in a single pass.

The cap arm transfer subsystem is mounted on a support bracket 400. A cap lift motor 222 operates to lift the cap arm lift fork 220 vertically with respect to the working surface 110. A cap translation motor 224 operates to move the cap lift fork 220 horizontally over the working surface 110.

A Soquel sensor 402 is a sensor located on the cap arm and used to detect different materials and/or disposables loaded into the instrument. The Soquel sensor 402 detects optical phase changes and is used to detect the presence, or absence, of caps in the loading station, tissues slides 290, caps in the QC station 218, and caps in the output station 216. The Soquel sensor 402 is accurate at making measurements in the micron range and may be coupled with optical systems to enhance the accuracy of focusing the objectives and the laser beam.

In an embodiment, the cap lift fork is moved by the cap translation motor 224 over a cap output station 216 on the working surface 110 to engage a cap and lifted up by a cap lift motor 222 with the cap engaged to the fork. The translation stage operates to move the working surface 110 along a horizontal plane, such that the cap is positioned over a selected section of the tissue sample slide 290. The cap lift motor 222 then operates to lower the cap to a designated site on the sample slide 290 and the cap translation motor 222 then operates to withdraw the cap lift fork 220 thereby disengaging the cap from the fork and leaving the cap in place over the selected tissue for performance of LCM.

Multiple caps may be positioned on a slide corresponding to one or more LCM sites on a tissue slide. Following a round of LCM on a slide, the capped slides 294 are positioned on the work surface 110 for further processing.

Following LCM, the cap transfer system picks up a cap from a capped slide and translates it to a QC station 218. A QC station 218 is a physical location on the work surface 110 where the cap can be placed for inspection purposes. An image file (tiff or jpeg) of the cells that were collected on the cap may be archived. Quantity of cells captured or "QC" may be performed to confirm the number of cells transferred or "captured" are within an acceptable fraction of the cells targeted. They can also look for and record any unwanted cells. A Non-Specific Removal (NSR) pad 410 may be optionally deployed as a means of removing non-specific or unwanted cells from the transfer film on the cap. The cap transfer system finally positions the cap on a disposable/microfuge tube.

Figure 5:
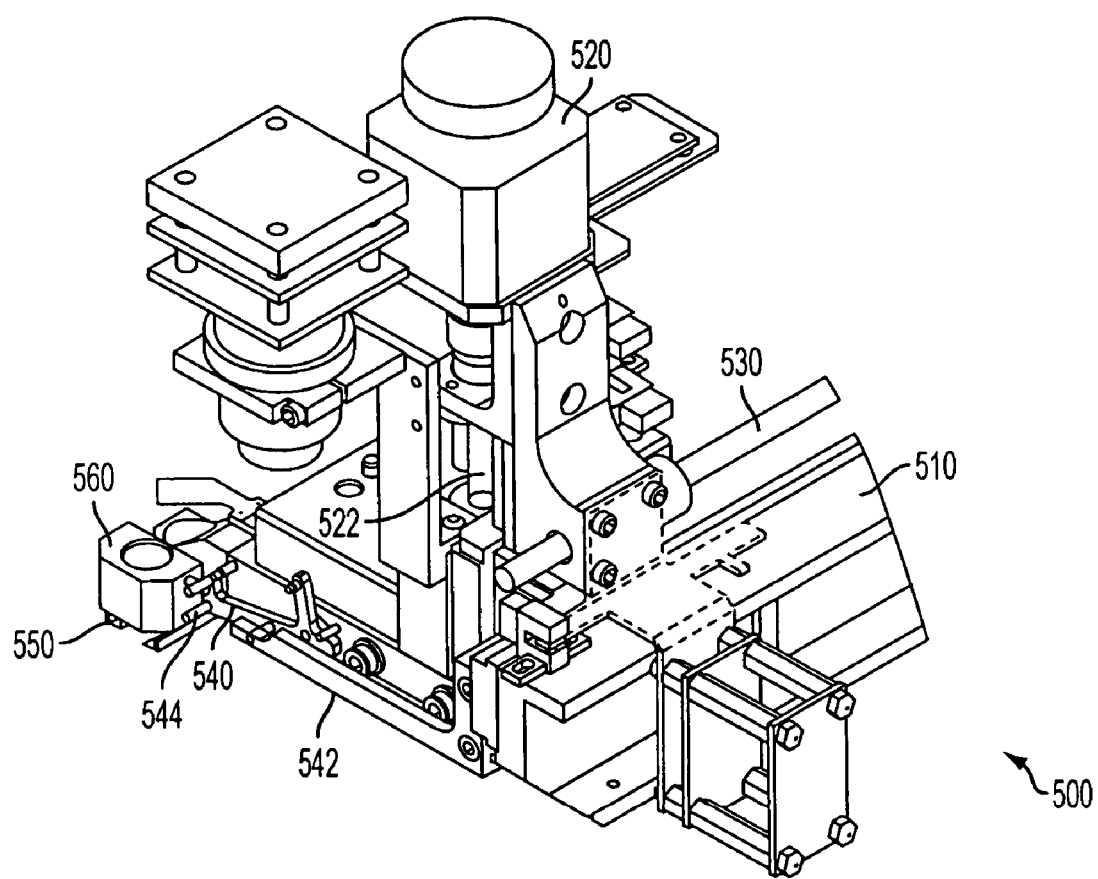
FIG. 5 illustrates a perspective view of a cap transfer system.

Turning now to FIG. 5, a perspective view of a cap transfer system 500 is depicted. The cap transfer system is mounted on a support beam 510 which in turn couples the cap transfer system to the LCM apparatus. A vertical drive motor 520 drives a vertical motion lead screw 522 to operate the lifting and lowering of the cap transfer system over the working surface. A cap translation motor (not shown in this figure) drives a horizontal motion lead screw 530 to operate a horizontal motion of the cap transfer system above the work surface as required for the translocation of caps. A lever actuator 542 is fixed to a horizontal support beam and operates to actuate a lever arm 540 which in turn actuates the motions of a cap pickup fork 550 and a cap weight 560 which are in turn involved in the precise positioning of the caps on various locations during the LCM process.

Figure 6:
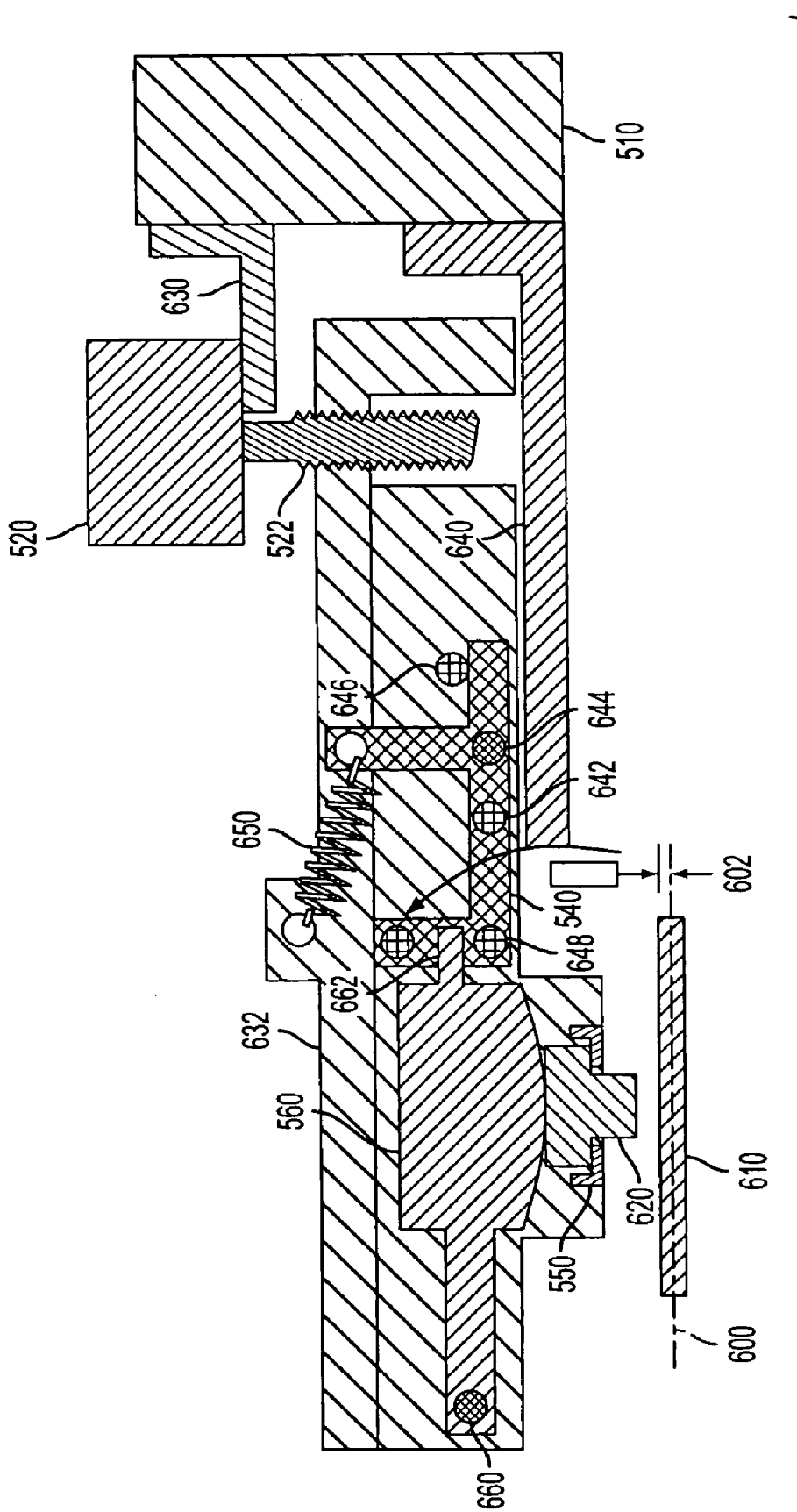
FIG. 6 illustrates a schematic diagram of a cap arm.

Turning to FIG. 6, a schematic diagram of a cap arm embodiment is illustrated. A kick bar 640 and motor bracket 630 are securely mounted on main support bar 510. A vertical lift motor 520 coupled to a vertical motion lead screw 522 is mounted on the motor bracket 630. The lead screw 522 is coupled to a horizontal support 632 and operates to lift or lower the horizontal support 632. Coupled by a spring 650 to the horizontal support 632 is a lever 540. The lever 540 includes several pins and stops 648 including a kick bar actuating pin 642 which, upon actuation, causes the lever 540 to pivot about an axis 644.

A cap weight 560 is coupled to the horizontal support 632 and also includes an arm 662 adjacent pins 648 of the lever 540. The cap weight 560 is able to pivot about an axis 660 and in one embodiment contacts the top of a cap 620 and exerts a force on the cap 620. A cap lift fork 550 is capable of sliding under the head of the cap 620 in certain configurations of the cap arm system.

A reference datum 600 is used to maintain a reference distance (d) 602 between the reference datum and the top of a cap support slide 610. The distance may be maintained electronically and is used as a reference for actuating the motions of the cap transfer arm.

(i) Cap Lift Sequence

Figure 7:
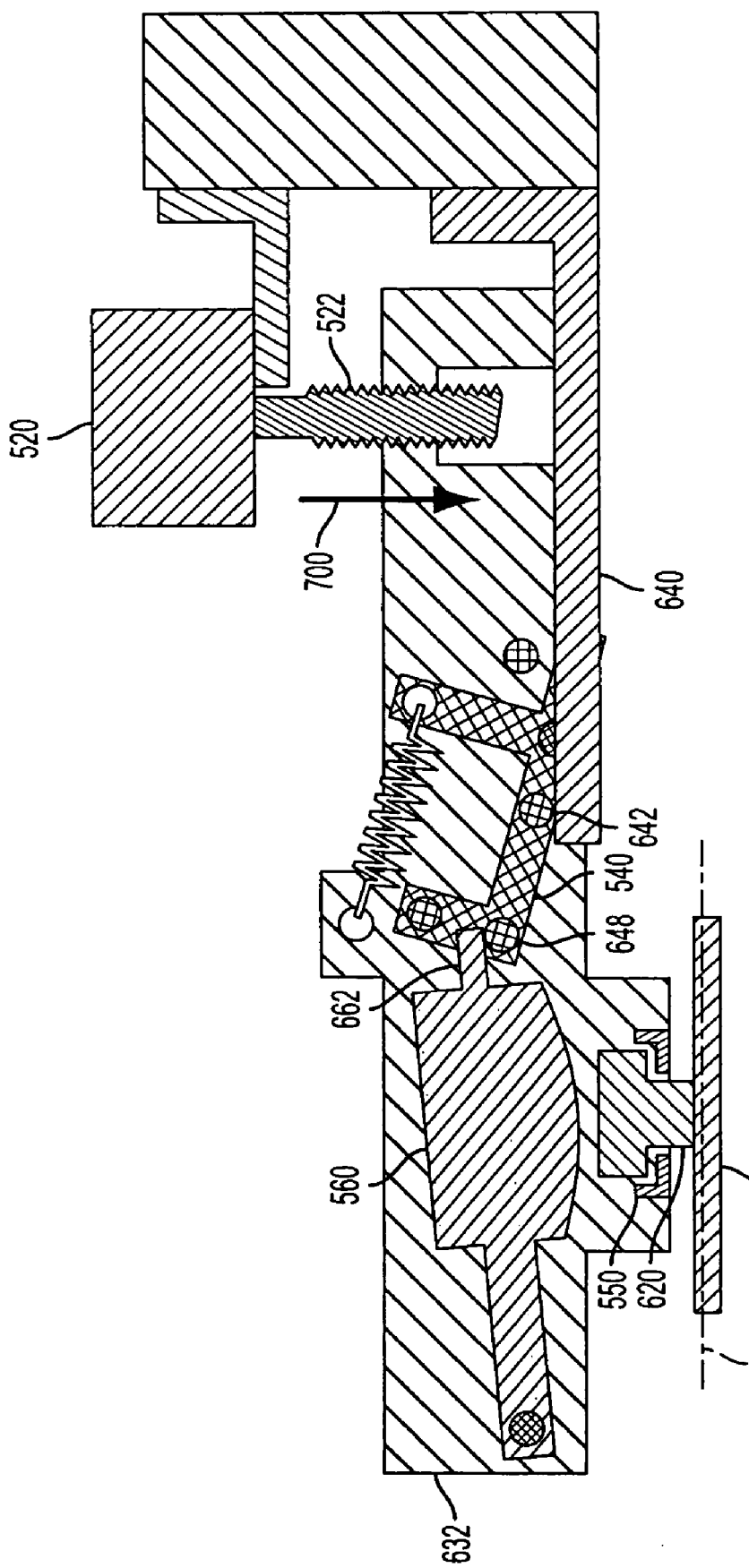
FIG. 7–8 illustrate a schematic diagram of an automated cap lift sequence mechanism.
Figure 8:
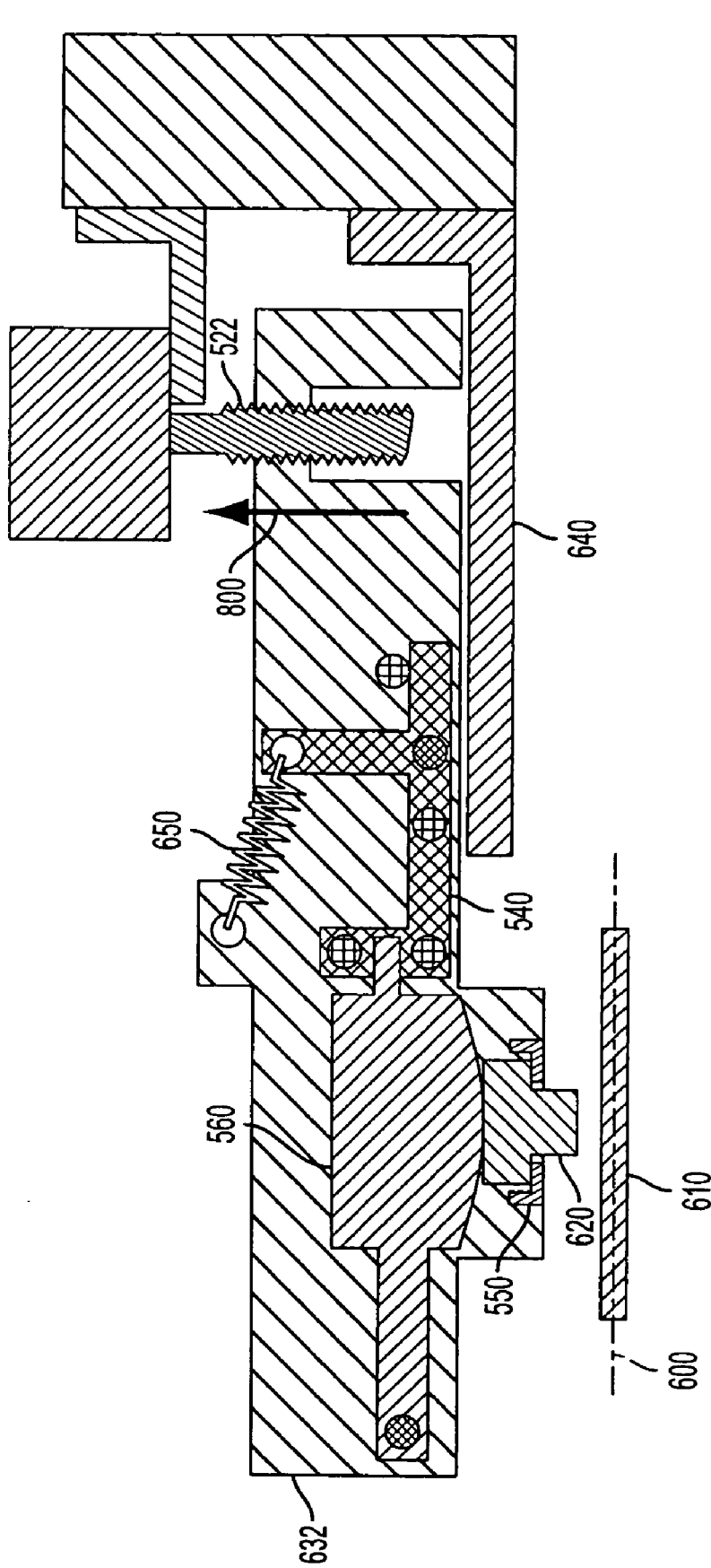

The automated manipulation of the film carrier cap is carried out by a transfer arm and actuator assembly, one embodiment of which is illustrated in the schematics of FIGS. 7 and 8. A first step of a cap lift sequence mechanism is schematically demonstrated in FIG. 7. The vertical lift motor 520 operates the vertical lead screw 522 to lower 700 the horizontal support 632. The lowering 700 of the horizontal support 632 causes the kick bar 640 to actuate the lever 540 by contacting the actuating pin 642 on the lever 540. Actuation of the lever 540 causes pins 648 on the lever which are adjacent an arm 662 of the weight to contact the arm 662 and lift the weight 560. The cap weight 560 is now lifted off the top of the cap 620.

Lowering 700 the horizontal support also causes the bottom of the cap 620 to contact the cap support slide 610. Arms of a cap lift fork 550 which are initially paced behind the cap 620 are now moved forward by a horizontal motion motor until the arms of the cap fork are positioned around the cap head. Without the force of the cap weight 560 on top, the translation of the fork arms is facilitated, thus enabling the fork 550 to engage the cap 620.

Turning now to the schematic on FIG. 8, the vertical motor then operates the vertical lead screw 522 to raise 800 the horizontal support 632. The cap 620 is lifted off the cap support slide 610 by the ascending cap lift fork 550. The kick bar 640 disengages the lever 540 and actuated by the operation of the spring 650 returns to its idle configuration which causes the cap weight 560 to be released and returned to its initial position on top of the cap 620. The cap is thus lifted and engaged by the cap transfer arm with the cap weight 560 securing its position.

(ii) Cap Transfer to Tissue Slide—Sequence

Figure 9:
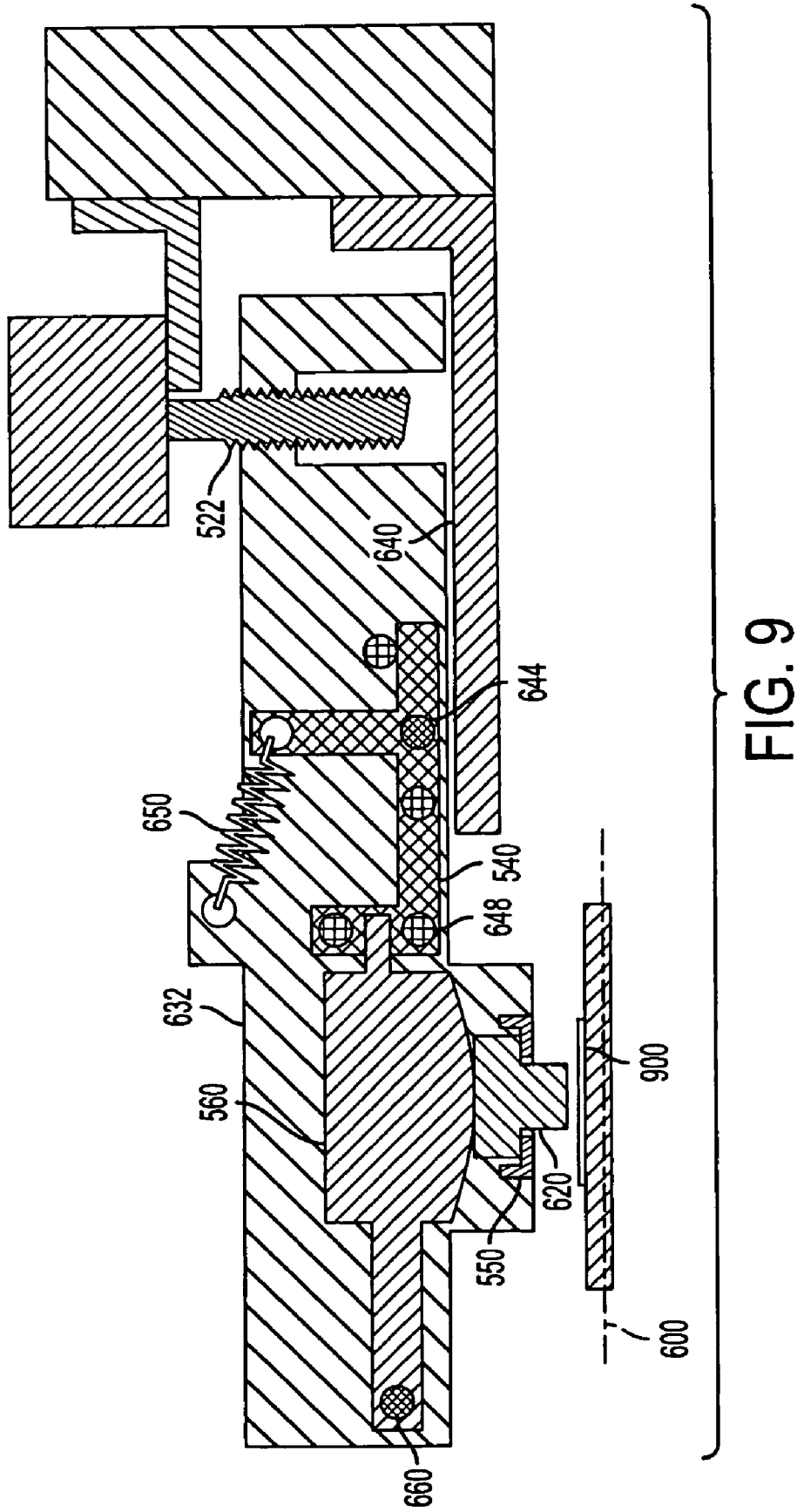
FIGS. 9–11 illustrate a schematic diagram of the mechanism by which a cap arm operates to transfer tissue sample to the transfer film.
Figure 10:
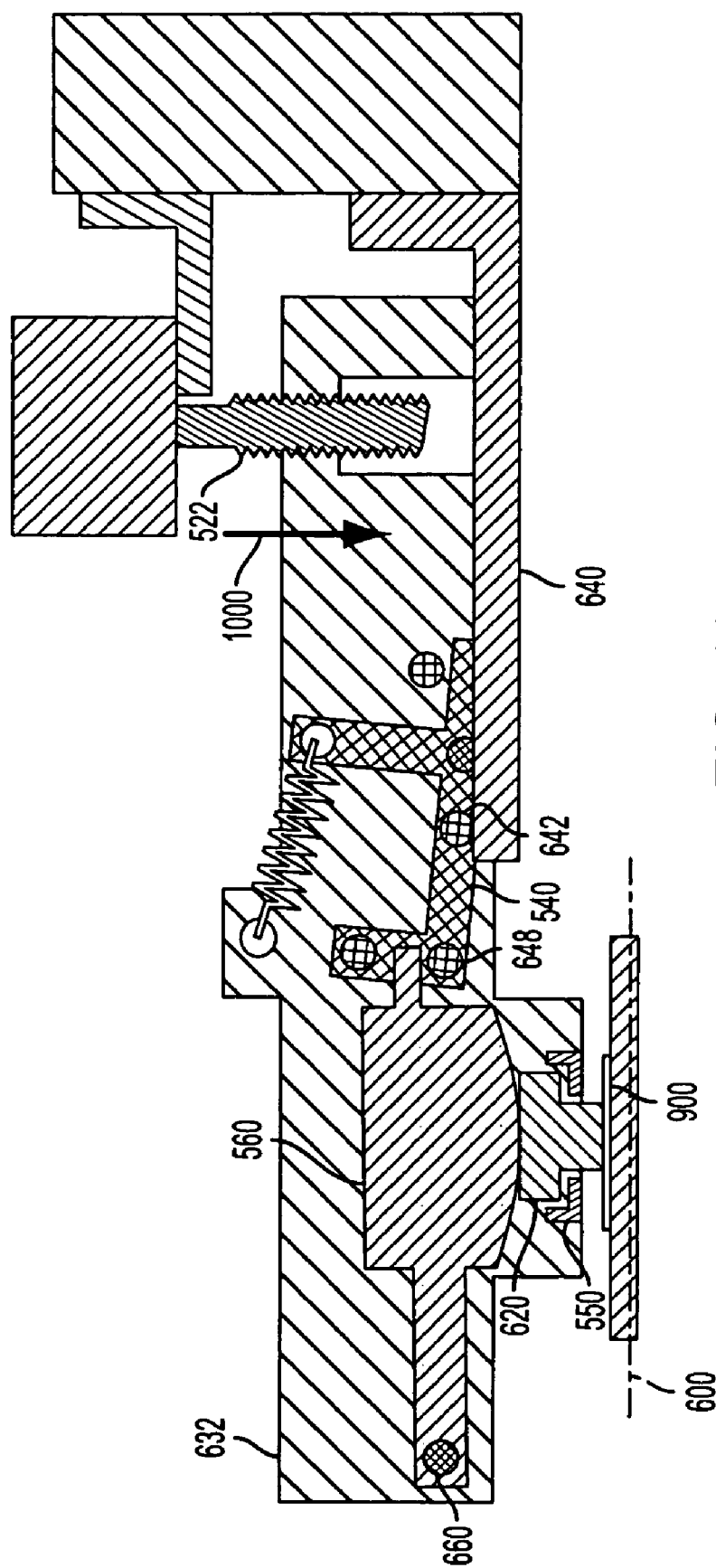
Figure 11:
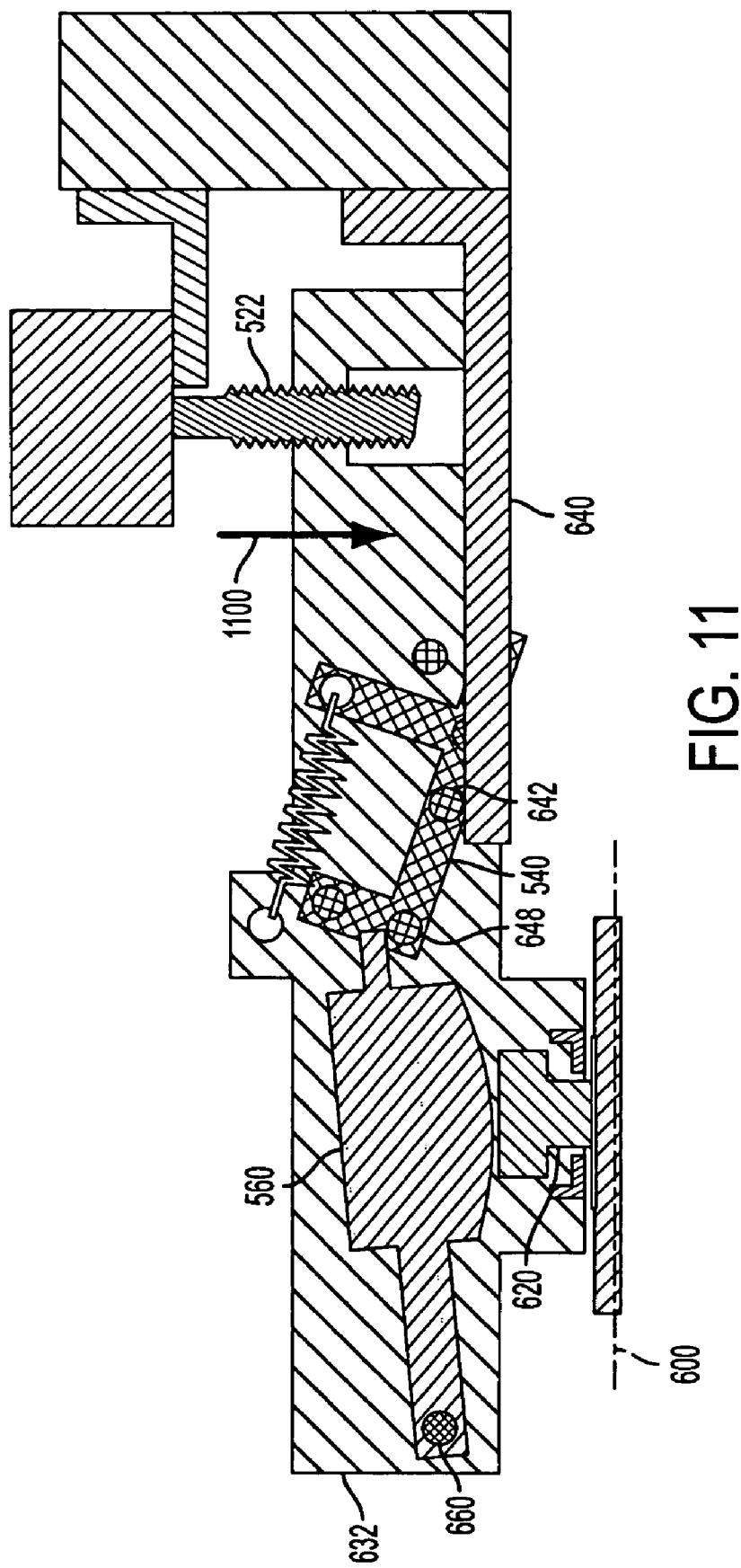

The mechanism for placement of the cap on a tissue sample on a slide is schematically displayed in FIGS. 9–11. A section of fluorescently-stained tissue for LCM is selected on the basis of fluorescence patterns upon excitation by an EPI/fluorescence laser 150, either fully automatically by a microprocessor controlled scanner or by an user from a video display of a live image of the fluorescent tissue sample. In response to such a selection, the translation stage of the work surface 110 and the cap transfer system 120 are manipulated by a controller such that a cap bearing arm of the cap transfer system 120 is positioned adjacent the work surface 110 with the cap 620 positioned above the selected section of the tissue 900. As depicted schematically in FIG. 9, the cap weight 560 rests on the cap 620 which is thereby secured in its position above a selected section of tissue 900. The tissue 900 is fixed on a slide at a position above the reference datum. The kick bar is disengaged from the lever 540 in this configuration.

Turning now to FIG. 10, a schematic configuration where the horizontal support 632 is partially lowered 1000 by operation of the vertical lead screw 522, is depicted. In this configuration, the kick bar actuating pin 642 on the lever 540 starts to contact the kick bar 640. However, the contact is not sufficient for the kick bar to pivot the lever 540 an adequate angle in order for the lever pin 648 to contact the weight 560. On the other hand, the horizontal support 632 is lowered sufficiently such that the cap 620 is seated on the tissue 900. The cap weight 560 seated on the top of the cap 620 ensures that the cap 620 is in firm contact with the tissue 900.

The weight 560 is free floating and permits the even application of pressure. For example, a weight of 30 grams can be used in the case where the total surface area of the LCM transfer film is approximately 0.26 square inches.

Turning next to FIG. 11, a schematic configuration where the horizontal support 632 is lowered 1100 even further by operation of the vertical lead screw 522, is depicted. In this configuration the kick bar 640 actuates the lever 540 by contacting the lever pin 642 and titling the lever 540 about its pivot axis 644. The lever pin 648 contacts the weight 560 and lifts it. The horizontal support 632 is also nearer the reference datum 600 which causes the slide to elevate the head of the cap 620 above the arms of the fork 550. The raised cap weight 560 thus allows the fork to be retracted leaving the cap placed precisely on top of the selected section of the tissue 900 on the slide. LCM may now be performed by a laser beam directed from above the cap and targeted at the specified section of the tissue sample.

(iii) Cap Transfer to Disposable—Sequence

Following the performance of a laser capture microdissection procedure a cap with selected tissue section attached is optionally transferred to a QC station for inspection for any unwanted cells. In addition, functions such as archiving image file (tiff or jpeg) of the cell collected on the cap, or confirmation that the number of cells transferred or "captured" are within an acceptable fraction of the cells targeted may also be performed at the QC station. The cap with the attached tissue sample is then translocated to an output station where the cap is placed on a "disposable" or a microcentrifuge tube (e.g., Eppendorf™) for recovering and analyzing the tissue samples.

Figure 12:
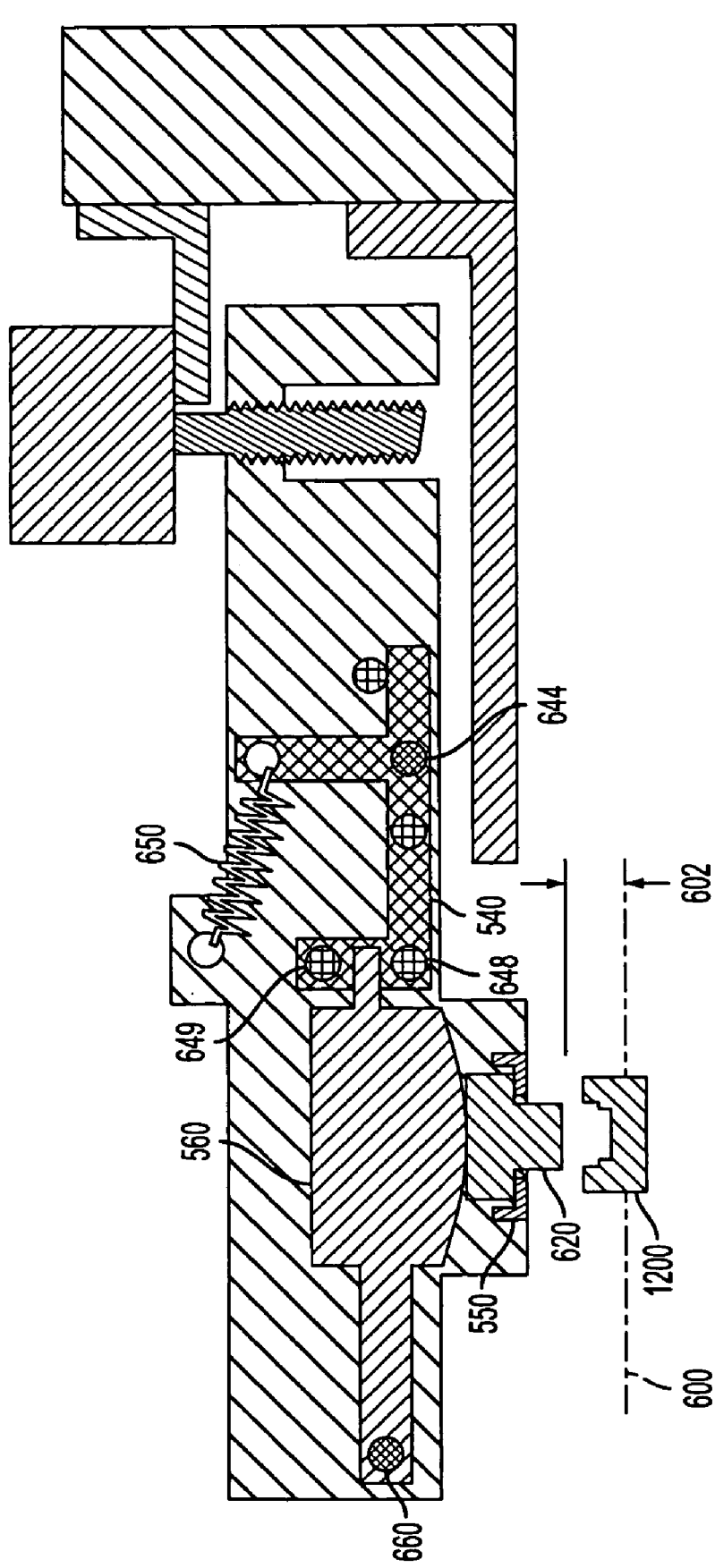
FIGS. 12–14 illustrate a schematic diagram of the mechanism by which a transfer of the cap containing the transfer film with the attached tissue sample to a reaction vessel is accomplished.
Figure 13:
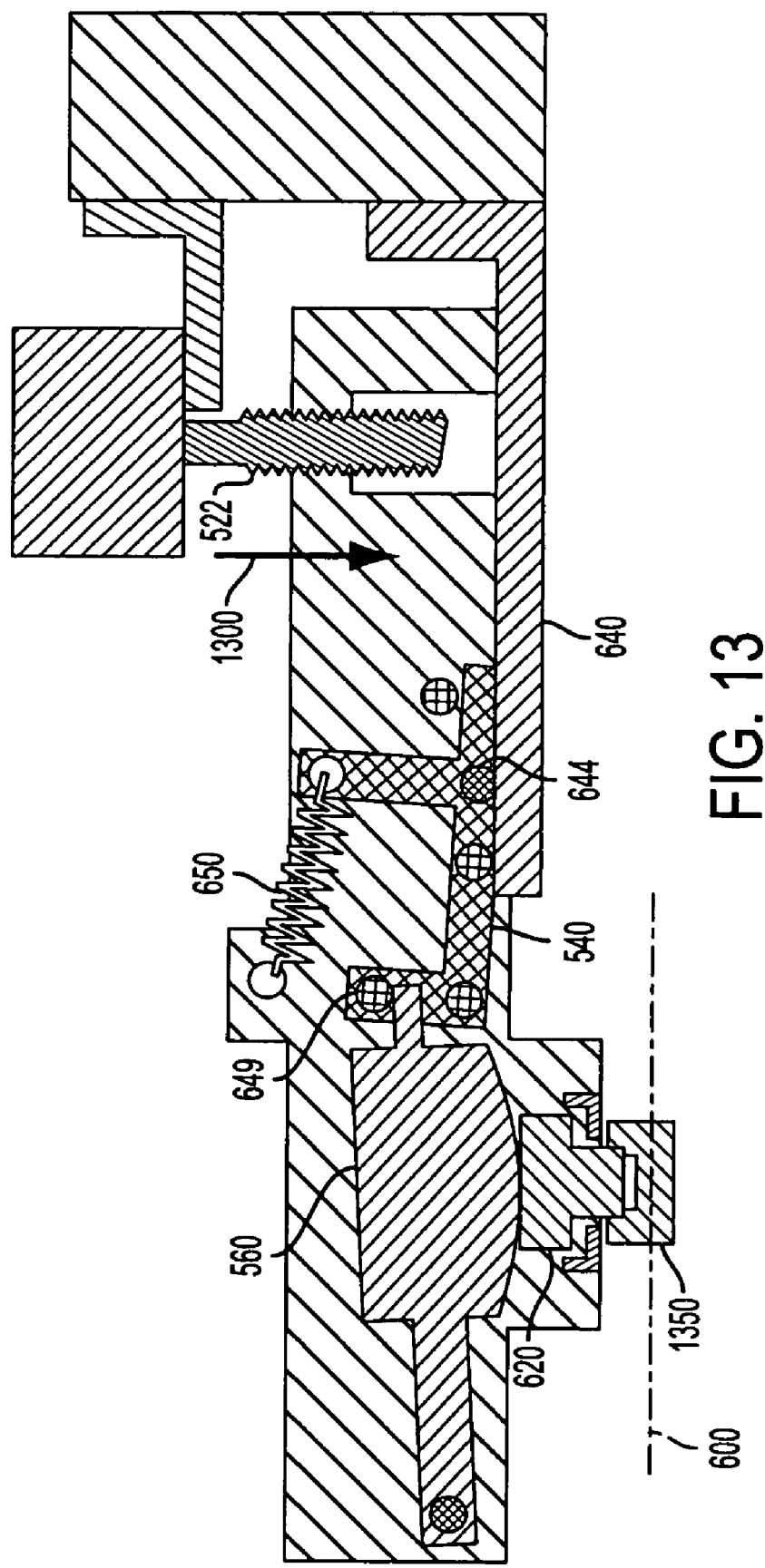
Figure 14:
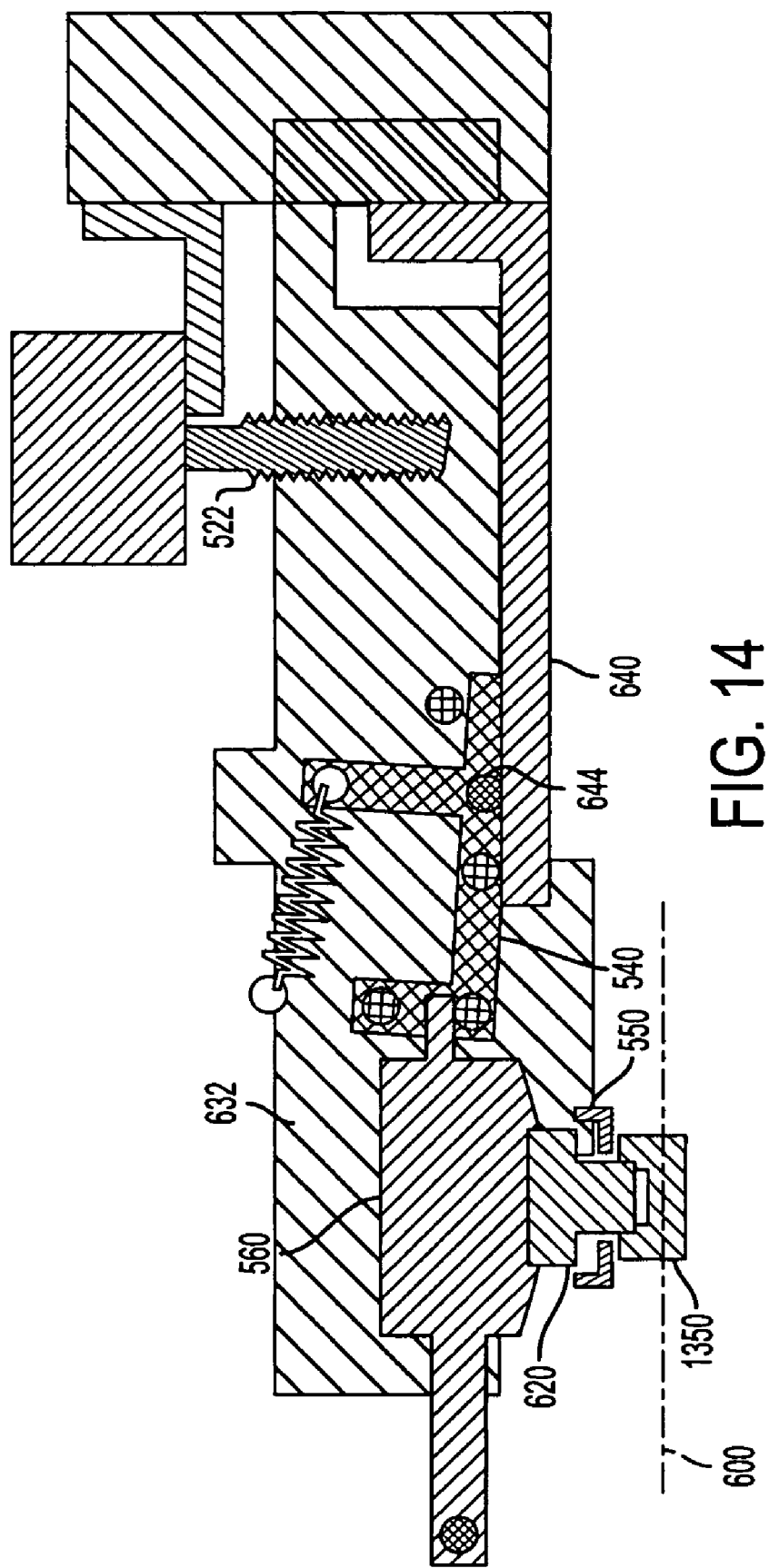

The cap transfer mechanism of the present invention automatically performs the procedure of inserting the cap into an aperture of a disposable/microfuge tube as schematically displayed in FIGS. 12–14.

Turning to FIG. 12, the cap transfer arm is translocated to a cap output where it is positioned in alignment with a disposable such that the cap 620 carrying a LCM film with attached tissue sample is positioned directly above a reaction vessel or disposable 1200. The disposable is selected such that the cap 620 fits snugly into its aperture and forms a tight seal when properly inserted into the disposable. Therefore, the cap requires some added force to be properly inserted into the aperture of the reaction vessel. In this configuration, the horizontal support is at a high point such that reference distance (d) 602 is large. The aperture of the reaction vessel 1200 is relatively high above the reference datum. The cap 620 is held in place by the cap weight 560 and the arms of the fork 550.

The next step of the transfer of the cap to the reaction vessel 1350 is schematically depicted in FIG. 13. The vertical lead screw 522 is operated to lower 1300 the horizontal support 632 such that the kick bar 640 actuates the lever 540 about its pivot axis 644. Since the starting position of the cap weight 560 is a resting position on the cap, the actuated lever causes the upper pin 649 to contact the weight 560. The force of the cap weight 560 against the upper pin 649 is counteracted by a force from a spring coupled to the lever 540 and the horizontal support 632. The spring force is translated to exert added pressure on the cap 620 by the cap weight 560 thereby forcing the cap into the reaction vessel 1350.

Turning next to FIG. 14, the cap transfer system is disengaged from the cap as depicted. With the cap 620 retained by its snug fit into the reaction vessel 1350, the arms of the fork 550 are retracted rearward thereby disengaging the cap 620. The rearward translation of the cap arm system actuated by the operation of the cap translation motor (not shown in this figure) also causes the cap weight 560 to slide off the cap 620. Since the horizontal support is in a lowered position, the lever 540 is in a pivoted configuration by engagement with the kick bar. The cap weight 560 therefore drops onto the lower pin 648 of the lever upon retraction of the fork arms 550. The cap 620 is retained on the reaction vessel 560.

All publications and patent applications mentioned in this specification are incorporated herein by reference to the same extent as if each individual publication or patent application were specifically and individually indicated to be incorporated by reference.

The above description is illustrative and not restrictive. Many variations will be apparent to those skilled in the art upon review of this disclosure. The scope of the invention should not be determined with reference to the above description, but instead should be determined with reference to the appended claims and the full scope of their equivalents.

What is claimed is:

1. An automated method of cap transfer in a laser microdissection instrument comprising:
    providing a work surface comprising a stage for performing laser microdissection;
    providing a cap transfer arm coupled to the work surface for removably engaging a laser microdissection cap;
    providing a controller coupled to a memory for receiving and storing an information corresponding to one or more locations on the work surface; and
    operating a movement of the cap transfer arm to place and remove a cap from one or more locations on the work surface.

2. The method of claim 1, wherein a location on the work surface is a site on a slide for performing laser microdissection on a tissue sample.

3. The method of claim 1, wherein a location on the work surface is a quality control inspection site.

4. The method of claim 1, wherein operating a movement of the cap transfer arm includes placing a cap with a transfer film on a tissue sample.

5. The method of claim 1, further comprising:
    providing a Soquel sensor for sensing the presence of at least one of caps in the loading station, tissues slides, caps in the quality control station, and caps in the output station.

* * * * *